United States Patent [19]

Moses

[11] Patent Number: 5,551,438
[45] Date of Patent: Sep. 3, 1996

[54] METHOD AND APPARATUS FOR DETERMINING BLOOD PRESSURE

[76] Inventor: John A. Moses, 80 Laslo Ter., Fairfield, Conn. 06430

[21] Appl. No.: 300,337

[22] Filed: Sep. 2, 1994

Related U.S. Application Data

[62] Division of Ser. No. 97,283, Jul. 26, 1993, Pat. No. 5,368,039.

[51] Int. Cl.[6] ......................................................... A61B 5/00
[52] U.S. Cl. ........................... 128/672; 128/680; 128/681; 128/687
[58] Field of Search ....................................... 128/677–687, 128/672

[56] References Cited

U.S. PATENT DOCUMENTS

| | | | |
|---|---|---|---|
| 3,102,534 | 9/1963 | Bigliano et al. | 128/672 |
| 3,123,068 | 3/1964 | Bigliano | 128/672 |
| 3,154,067 | 10/1964 | Stenstrom et al. | 128/677 |
| 3,219,035 | 11/1965 | Pressman et al. | 128/672 |
| 3,527,204 | 9/1970 | Lem et al. | 188/677 |
| 3,880,145 | 4/1975 | Blick | 128/677 |
| 3,903,872 | 9/1975 | Link | 128/681 |
| 3,903,873 | 9/1975 | Royal et al. | 128/677 |
| 3,926,179 | 12/1975 | Petzke et al. | 128/672 |
| 3,983,452 | 9/1976 | Birnbaum | 128/680 |
| 4,009,709 | 3/1977 | Link et al. | 128/681 |
| 4,030,484 | 6/1977 | Kuska et al. | 128/672 |

(List continued on next page.)

FOREIGN PATENT DOCUMENTS

WO79/00294 11/1978 WIPO.
WO88/03777 11/1987 WIPO.

OTHER PUBLICATIONS

"Evaluation of Arterial Tonometry for Noninvasive Continuous Blood Pressure Monitoring During Anesthesia" Kemmotsu et al. Anesthesiology V71, No. 3A, Sep. 1989.

"Arterial Tonometry: Review and Analysis", G. Drzewiecki et al., J. Biomechanics, vol. No. 2, pp. 141–152 (1983).

"The Meaning of the Point of Maximum Oscillations in Cuff Pressure in the Indirect Measurement of Blood Pressure. Part 1" J. Posey et al., Cardiovascular Research Center Bull. Jul.–Sep. 1969.

"Characterization of the Oscillometric Method for Measuring Indirect Blood Pressure" L. Geddes et al. Annals of Biomedical Engineering, vol. 10, pp. 271–280, 1982.

"The Indirect Measurement of Mean Blood Pressure in the Horse", L. Geddes et al., The Southwestern Veterinarian, Summer, 1970.

"A Transducer for the Continuous External Measurement of Arterial Blood Pressure" G. Pressman et al IEEE Transactions on Bio–Medical Electronics.

Primary Examiner—Angela D. Sykes
Assistant Examiner—Robert L. Nasser, Jr.
Attorney, Agent, or Firm—Perman & Green

[57] ABSTRACT

A transducer assembly (12) is applied to the surface of the body beneath an inflatable cuff (10). Transducers (12c) are disposed upon a substrate (12a) and may include from one to some large number of transducers suitable for detecting an oscillation resulting from arterial blood flow within a partially occluded artery. Each transducer (12c) can be of large size, relative to an artery (16), to eliminate a requirement that the transducer be accurately placed over and maintained upon the artery. The substrate can be provided to have a surface with a radius of curvature selected to approximate a curvature of the extremity to which the transducer array is applied. The cuff pressure is increased to a level above the systolic pressure of the individual and then gradually reduced. Oscillations are sensed by one or more of the transducers as the cuff pressure is decreased. When the systolic pressure is reached, the sensed oscillations begin to increase in amplitude until they reach a maximum amplitude. The cuff pressure at the point of maximum amplitude is correlated with the Mean Arterial Pressure of the subject. Methods for accomplishing a sub-diastolic continuous measurement cycle and a Mean Arterial Pressure monitoring cycle are also provided.

11 Claims, 7 Drawing Sheets

U.S. PATENT DOCUMENTS

| | | | |
|---|---|---|---|
| 4,068,654 | 1/1978 | Paavola et al. | |
| 4,074,711 | 2/1978 | Link et al. | |
| 4,185,621 | 1/1980 | Morrow | 128/672 |
| 4,269,193 | 5/1981 | Eckerle | 128/672 |
| 4,295,471 | 10/1981 | Kaspari. | |
| 4,307,727 | 12/1981 | Haynes | 128/672 |
| 4,349,034 | 9/1982 | Ramsey, III | 128/672 |
| 4,423,738 | 1/1984 | Newgard. | |
| 4,427,013 | 1/1984 | Nunn et al. | 128/681 |
| 4,489,731 | 12/1984 | Baumberg. | |
| 4,543,962 | 10/1985 | Medero et al. | 188/680 |
| 4,653,506 | 3/1987 | Romanovskaya. | |
| 4,790,325 | 12/1988 | Lee | 128/677 |
| 4,823,802 | 4/1989 | Romanovskaya | 128/688 |
| 4,860,760 | 8/1989 | Miyawaki et al. | 128/681 |
| 4,880,013 | 11/1989 | Chio | 128/681 |
| 4,924,871 | 5/1990 | Honeyager | 128/687 |
| 4,951,679 | 8/1990 | Harada | 128/687 |
| 4,984,577 | 1/1991 | Frankenreiter | 128/681 |
| 4,987,900 | 1/1991 | Eckerle et al. | 128/687 |
| 4,993,422 | 2/1991 | Hon et al. | 128/687 |
| 4,995,399 | 2/1991 | Hayashi et al. | 128/680 |
| 5,000,187 | 3/1991 | Higuchi et al. | 128/681 |
| 5,005,581 | 4/1991 | Honeyager | 128/687 |
| 5,031,630 | 7/1991 | Hirano et al. | 128/686 |
| 5,033,471 | 7/1991 | Yokoe et al. | 128/681 |
| 5,065,765 | 11/1991 | Eckerle et al. | 128/681 |
| 5,094,245 | 3/1992 | Shirasaki | 128/680 |
| 5,103,830 | 4/1992 | Shinomiya | 128/681 |
| 5,165,416 | 11/1992 | Shinoda et al. | 128/681 |
| 5,172,696 | 12/1992 | Souma | 128/687 |
| 5,183,050 | 2/1993 | Kawamura | 128/687 |
| 5,335,665 | 8/1994 | Suzuki | 128/680 |
| 5,337,750 | 8/1994 | Walloch | 128/681 |

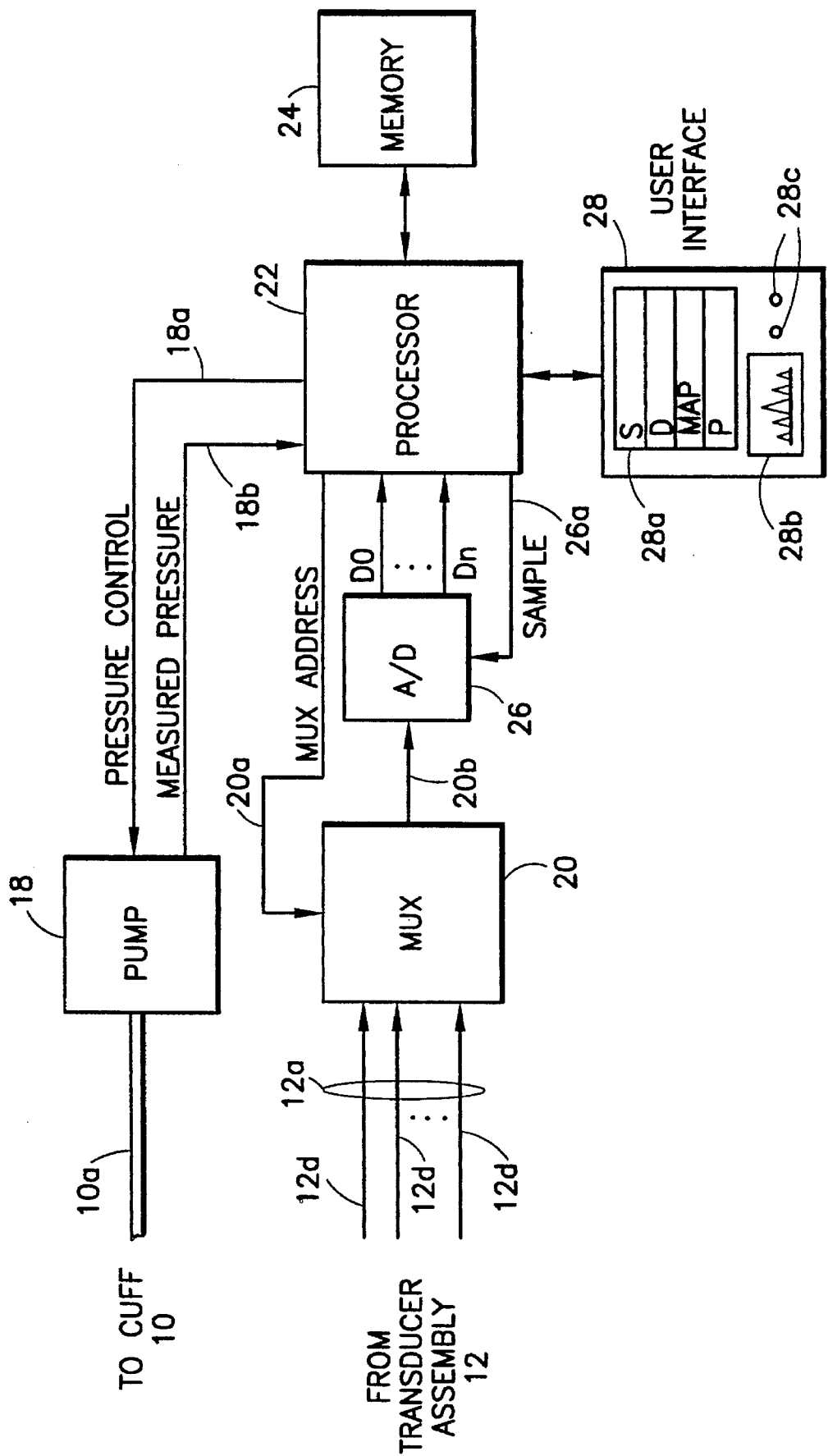

METHOD AND APPARATUS FOR DETERMINING BLOOD PRESSURE

This is a divisional of application Ser. No. 08/097,283 filed on Jul. 26, 1993, now U.S. Pat. No. 5,368,039.

FIELD OF THE INVENTION

This invention relates generally to non-invasive methods and apparatus for measuring blood pressure.

BACKGROUND OF THE INVENTION

Blood is circulated through the body by the contraction of the heart. Referring to FIG. 1, which illustrates a blood pressure wave obtained by an invasive technique, when the heart contracts it pumps blood into the arteries. This generates, typically, a maximum pressure of 120 mm Hg, which is referred to as the systolic pressure. When the contraction terminates, the pressure falls, typically, to 80 mm Hg, which is referred to as the diastolic pressure. The dashed line, designated A, generally indicates the significantly reduced pressure waveform that would be measured at the surface of the skin, as opposed to within the artery itself.

The mean blood pressure, often referred to as the Mean Arterial Pressure (MAP), is an average blood pressure over the entire contraction cycle. The MAP is, however, not the average of 120 and 80, in that the blood pressure is nearer to the diastolic pressure during most of the contraction cycle. As a result, the MAP is typically about 90 mm. Hg. The determination of the MAP is considered to be important, in that it generally provides more information concerning the overall functioning of the subject's circulatory system than do measurements of only the systolic and diastolic pressures.

The systolic and diastolic pressures are typically measured by wrapping a blood pressure cuff around an extremity containing an artery, inflating the cuff to a predetermined pressure above the systolic pressure, thereby occluding the artery, and reducing the pressure gradually allowing increased flow through the artery. Oscillations resulting from arterial blood flow through the partially occluded artery are sensed in some manner for an entire blood pressure measuring cycle.

The most common method for measuring blood pressure indirectly is with a sphygmomanometer and stethoscope. Advantages of the sphygmomanometer and stethoscope include simplicity and low cost. However, the procedure is relatively inaccurate, and produces only a limited amount of diagnostic information.

The procedure by which a sphygmomanometer is utilized to determine blood pressure is relatively simple. A collapsed, inflatable blood pressure cuff is first placed around a subject's arm. Pressure in the cuff is then increased to a level of about 30 mm. Hg. above a point at which the palpable pulse disappears. As the cuff is deflated, observations may be made either by palpation or auscultation. The point at which the pulse can be felt is recorded from the manometer as the systolic pressure.

The auscultatory method is usually preferred to the technique described above. With this method, vibrations from the artery under pressure, called Korotkoff sounds, are used as indicators.

To determine blood pressure using the auscultatory method, the bell or diaphragm of a stethoscope is pressed lightly over a brachial artery while the cuff is slowly deflated. The pressure readings begin at the time the Korotkoff sounds first become audible. As the cuff is deflated further, the sounds become louder for a brief period. The sounds then become muffled and finally disappear. The systolic blood pressure is the point at which the Korotkoff sounds become audible, and the diastolic blood pressure is the point at which the sounds cease to be heard.

There are several other known methods for accomplishing the measuring of the systolic and the diastolic pressures. Two conventional methods, that rely on the use of electronic components, are known in the art as oscillometry and tonometry.

In oscillometry, the oscillations resulting from arterial blood flow through the partially occluded artery are transmitted as pressure variations through the cuff and tubings to a sensitive pressure transducer located within a monitor. However, in that the pressure transducer must be highly sensitive, the slightest movement of the subject can give rise artifacts which reduce the accuracy of the measurement. As a result, artifact detection and rejection circuits may be required to be included within the monitor. Furthermore, the oscillometric method typically requires a stepwise reduction of cuff pressure. In addition, blood pressure measurement may not be possible at all if the subject's blood pressure is below a threshold value.

In tonometry a transducer is placed directly over a superficial artery, such as the radial artery, and is compressed against an underlying bone with a predetermined pressure. Oscillations resulting from arterial blood flow through the artery are converted to electrical signals by the transducer and are subsequently detected. In practice, the transducer is smaller than the diameter of the artery. As a result, the tonometric sensor must be positioned very accurately over the artery, and must also partially compress the artery. As a result, even a small misalignment makes it difficult or impossible to accurately measure blood pressure. Furthermore, accurate calibration of the tonometric system is typically necessary.

U.S. Pat. No. 4,427,013 describes the use of a determination of an increase and a decrease in the rate of a rise and a fall, respectively, of a blood pressure waveform to determine the systolic and the diastolic pressures. In U.S. Pat. No. 4,860,760 there is described the use of a first fixed threshold, referenced to a peak blood pressure, to indicate the systolic pressure, and a second fixed threshold to indicate the diastolic pressure.

These and other U.S. Patents of interest to the teaching of this invention are described below.

U.S. Pat. No. 5,031,630, issued Jul. 16, 1991, entitled Automatic Blood Pressure Measuring Apparatus, describes a cuff 10 having six piezoelectric sheets 18–28 disposed on a cuff surface that contacts the body of the patient. Sheets 18–22 are arranged to detect proximal artery sounds, while sheets 24–28 are located to detect Korotkoff sounds transmitted from the artery to a middle area of the cuff (col. 3, line 48–col. 4, line 3). Signals generated by the sheets 18–28 are digitized and applied to a CPU 34, as is the output of a cuff pressure sensor 36 (col. 4, lines 4–24). The sheets (18–22) are monitored to select an optimum sensing sheet, after which the sheet (24–26) that is aligned with the selected sheet (18–22) is also selected (col. 5, lines 14–44). The selected piezoelectric sheets are used to monitor Korotkoff sounds, which are used in conjunction with cuff pressure to determine blood pressure (col. 6, lines 4–48). The size of the individual (cuff-mounted) piezoelectric sheets is not disclosed (i.e., whether they are smaller or larger than the artery).

U.S. Pat. No. 5,165,416, issued Nov. 24, 1992, entitled "Continuous Blood Pressure Monitoring System Having a Digital Cuff Calibration System and Method", describes the use of a tonometric sensor 10 and a digital cuff 20. Both the sensor 10 and cuff 20 receive a pressurized fluid (col. 2, lines 53–54). The cuff 20 is positioned downstream of sensor 10 (col. 4, lines 38–42). A calibration sensor 22 can be added to the cuff 20. The sensor 22 can be a microphone for detecting Korotkoff sounds, or may be an optical sensor (col. 4, lines 47–57).

U.S. Pat. No. 4,880,013, issued Nov. 14, 1989, entitled "Method and Apparatus For Determining Blood Pressure and Cardiovascular Condition" describes the use of a pressure transducer 16 and a cuff 10. Both are said to be affixed to the patent (col. 4, lines 36–37). A data stream is obtained from the pressure transducer 16, the data stream including both pressure data and pulsation signal data. Systolic maximum points and diastolic minimum points are determined. Two methods of determining Mean Arterial Pressure (MAP) are also disclosed; specifically a "midpoint method" and a "mathematical calculation method". A procedure for operating the cuff and pressure transducer is described at col. 11, lines 5–65. It is noted that this patent does not provide any specifics as to how and where the transducer is affixed to the patient. At col. 8, lines 32–36 it is stated that the pressure transducer may be that supplied with a known type of blood pressure monitor. As indicated at col. 3, lines 6–23, this known type of device appears to operate on the oscillometric, as opposed to the tonometric, principle.

U.S. Pat. No. 4,295,471, issued Oct. 20, 1981, entitled "Non-Invasive Vascular Waveform Transducer and Apparatus" describes the use of an inflatable cuff 10 that includes a transducer 30. The transducer is located near a blood vessel to be monitored when the cuff is installed (col. 3, lines 53–62). The transducer 30 is used to detect Korotkoff sounds as the cuff is deflated (col. 4, lines 7–12). A dual sensing approach, described at col. 5, lines 21–40, is used to reject common mode signals (col. 5, line 54 to col. 6, line 16). The determination of MAP is described at col. 14, lines 38–54. A continuous display of an arterial waveform is described at col. 15, line 64 to col. 16, line 12. All embodiments of the transducer 10 appear to be circular in shape (FIGS. 2a, 5a, 5b, 5c), and not shaped to generally conform to the extremity of the patient.

U.S. Pat. No. 5,103,830, issued Apr. 14, 1992, entitled "Electronic Sphygmomanometer", describes an electronic sphygmomanometer that uses both the Korotkoff and the oscillometric methods. A cuff 1 has a Korotkoff sound sensor disposed on a "periphery" of the cuff (col. 6, lines 10–23), and a pressure sensor 21 is connected to the cuff 1.

U.S. Pat. No. 4,653,506, issued Mar. 31, 1987, entitled "Method of Indirect Measurement of Arterial Tension and a Device for Pulse Wave Registration", describes the use of a cuff 3 under which a device 9 is applied to a patient's body. The passing of a blood pulse wave under the device 9 is converted to an electrical signal by a piezo-sensitive cell 17 (col. 6, liens 13–19). Cuff pressure is monitored by a pressure gauge 11. The cuff pressure does not appear to be converted to an electrical signal, and no means is disclosed for correlating signals received from the device 9 with cuff pressure.

U.S. Pat. No. 4,951,679, issued Aug. 28, 1990, entitled "Pulse Wave Detecting Apparatus Having Placement-Condition Detecting Means", describes a tonometric-type device that includes a pulse wave detecting probe 16 that is fixed with a band 14 fastened around a patient's arm. The probe 16 is pressurized with a fluid for urging a diaphragm 22 toward the surface of the arm (col. 3, line 37 to col. 4, line 9).

U.S. Pat. No. 5,033,471, issued Aug. 23, 1991, entitled "Method and Apparatus Measuring Blood Pressure", is also directed to a tonometric-type device that appears to be similar to that described above with respect to U.S. Pat. No. 4,951,679 (see col. 6, line 56 to col. 7, line 55).

U.S. Pat. No. 5,172,696, issued Dec. 22, 1992, entitled "Photoelectric Sphygmomanometer of Volume Oscillometric Method-Type", describes a photoelectric sphygmomanometer of a "volume oscillometric" type. A cuff 1 is fastened to the wrist or fingertip of a patient. A pressure sensor 6 senses cuff pressure. A pulsation sensor 8, located inside the cuff, includes a LED 8a and phototransistor 8b for irradiating arterial blood and detecting light reflected from the arterial blood, respectively (col. 4, lines 10–36). Measurements of cuff pressure and pulsation signals are used to determine systolic, diastolic, and mean blood pressure (col. 8, lines 14–26). The use of a tonometric, under-cuff sensor, that may be shaped to conform to the extremity of the patient, is not disclosed.

U.S. Pat. No. 4,924,871, issued May 15, 1990, entitled "Motion Artifact Detection for Continuous Blood Pressure Monitor Transducer", describes a tonometric-type device that includes an array of individual pressure sensitive transducers 22A–22E, all of which are small relative to the diameter of an artery (FIG. 4, col. 3, line 59–col. 4, line 22). A change in pressure within a pressurizable chamber 40 is detected and interpreted to indicate motion of the patient. When motion is detected, data collection is interrupted (col. 5, line 55 to col. 6, line 31).

U.S. Pat. No. 4,860,760, issued Aug. 29, 1989, entitled "Electronic Blood Pressure Meter Incorporating Compensation Function for Systolic and Diastolic Blood Pressure Determinations", describes an oscillometric-type device wherein a cuff 2 is connected to a pressure sensor 11 (col. 10, lines 16–66).

Also of interest is U.S. Pat. No. 3,527,204, issued Sep. 8, 1970, which describes at col. 4, lines 6–10 the use of a transducer 111 which may be a microphone. The microphone is said to be placed under a cuff when blood pressure is measured using an auscultatory method.

Other patents of interest to this invention include the following. A first group of patents are generally related to oscillometric-type determinations: U.S. Pat. Nos. 5,001,187, 4,427,013, 3,903,872 (which provides a cuff-mounted pressure transducer), 4,543,962, 4,349,034, 4,009,709, 4,984, 577, 4,995,399 and 4,074,711. A second group of patents are generally related to tonometric-type determinations: U.S. Pat. Nos. 3,880,145, 4,269,193, 4,223,738, 4,987,900, and 5,005,581 (all of which employ multiple sensors). Also of interest are U.S. Pat. Nos. 4,993,422, 3,102,534, 3,123,068, 3,154,067 (which provides a strain gauge), 3,903,873, 3,926,179, 4,185,621, 4,034,484 and 4,307,727.

Also of interest is a pulse rate monitor shown in U.S. Pat. Nos. 4,489,731, a cuff-less blood pressure measuring device shown in 4,068,654, and the systems described in the Abstracts of WO 79/00294 and WO 88/03777.

An invasive blood pressure measuring system that is capable of measuring the mean arterial pressure is described in U.S. Pat. No. 3,893,452.

Also of interest is an article entitled "Evaluation of Arterial Tonometry for Noninvasive Continuous Blood Pressure Monitoring During Anesthesia", Anesthesiology, V71, No. 3A, September 1989 (O. Kemmotsu, et al.); an article entitled "Arterial Tonometry: Review and Analysis", J. Biomechanics, Vol. 16, No. 2, pp. 141–152, 1983 (Gary M. Drzewiecki, et al.); an article entitled "The Meaning of the Point of Maximum Oscillations in Cuff Pressure in the Indirect Measurement of Blood Pressure, Part I.", Cardiovascular Research Center Bulletin, Vol. 8, No. 1, July–September, 1969 (J. A. Posey, et al.); an article entitled "Characterization of the Oscillometric Method for Measuring Indirect Blood Pressure", Annals of Biomedical Engineering, Vol. 10, pp. 271–283, 1982 (L. A. Geddes, et al.); an article entitled "The Indirect Measurement of Mean Blood Pressure in the Horse", The Southwestern Veterinarian, pp. 289–293, Summer 1970 (L. A. Geddes, et al.); and an article entitled "A Transducer for the Continuous External Measurement of Arterial Blood Pressure", IEEE Transactions on Bio-Medical Electronics", pp. 73–81, 1963, (G. L. Pressman et al.).

SUMMARY OF THE INVENTION

It is one object of this invention to provide a non-invasive method and apparatus and method that overcomes the problems encountered with the use of both the oscillometric and tonometric approaches.

It is another object of this invention to provide a non-invasive method and apparatus and method that combines elements from the oscillometric and tonometric approaches to yield a technique that is superior to both.

It is a further object of this invention to provide a transducer assembly for use in obtaining a blood pressure measurement, the transducer assembly being comprised of a substrate having a curved surface and one or more pressure transducers located on the curved surface.

It is another object of this invention to provide a method to determine the Mean Arterial Pressure of a subject in a non-invasive and accurate manner.

A further object of this invention is to provide a non-invasive technique to monitor the Mean Arterial Pressure over a period of time.

A still further object of this invention is to provide a non-invasive technique to monitor the blood pressure over an extended period of time, while employing a cuff pressure that is less than the diastolic pressure of a subject.

The above-described and other problems are overcome, and the objects are realized, by an apparatus and methods for measuring blood pressure in accordance with the teaching of this invention. The apparatus includes a pressure sensing device or transducer that is placed over the skin of an extremity near an artery. For example, the transducer may be placed on the upper arm near the brachial artery. An inflatable cuff is wrapped around the extremity over the sensor in a manner similar to the application of a conventional blood pressure cuff.

Operation includes inflating of the cuff to a predetermined pressure, and then correlating the cuff pressure to the amplitude of oscillations measured by the transducer while the cuff pressure is gradually reduced from a level above the systolic to below the diastolic pressure. The cuff pressure at which the amplitude of oscillations is a maximum is correlated with the MAP. The systolic and diastolic pressures are determined, in a first embodiment of the invention, by comparing measured oscillation amplitudes with other measured amplitudes while adding or subtracting, respectively, a predetermined amplitude increment.

In another embodiment of the invention the oscillations are collected over an entire blood pressure measurement cycle, a maximum oscillation amplitude is determined, the systolic and diastolic pressures are determined by correlating the cuff pressure at points where oscillations are within a predetermined percentage of the maximum amplitude, and the Mean Arterial Pressure is determined by correlating the cuff pressure at the time of the oscillation having the maximum amplitude.

The blood pressure measurement is made non-invasively, that is, the transducer comes into contact with the surface of the body but does not penetrate the skin into deeper body tissues.

The present invention provides an apparatus and a method of determining blood pressure by applying a blood pressure cuff around an extremity containing an artery, inflating the cuff to a predetermined pressure above the systolic pressure, thereby occluding the artery, and reducing the pressure gradually allowing increased flow through the artery.

A transducer array is first applied to the surface of the body beneath the cuff. The transducer array is disposed upon a substrate and may include from one to some large number of transducers suitable for detecting an oscillation resulting from arterial blood flow within a partially occluded artery. Each transducer is preferably of large size, relative to the artery, to eliminate a requirement that the transducer be accurately placed over and maintained upon the artery. The substrate may be provided to have a surface with a radius of curvature selected to approximate a curvature of the extremity to which the transducer array is applied.

The cuff pressure is increased to a level above the systolic pressure of the individual and then gradually reduced. Oscillations are sensed by one or more of the transducers of the transducer array as the cuff pressure is decreased. When the systolic pressure is reached, the sensed oscillations begin to increase in amplitude until they reach a maximum amplitude. The cuff pressure at the point of maximum amplitude is correlated with the MAP of the subject. The amplitude of the oscillations then begin to decrease until the cuff pressure is approximately equal to the diastolic blood pressure, at which time the oscillations fall below a predetermined minimum amplitude.

The cuff pressure and the amplitude of oscillations may be registered by a monitor for an entire blood pressure monitoring cycle for subsequent analysis. Alternatively, the analysis may be carried out in real time, i.e., during the blood pressure measurement cycle. In either case, the cuff pressure at the maximum amplitude of oscillations is determined and reported as the mean arterial blood pressure.

The teaching of this invention is also extendable to the continuous measurement of blood pressure over an interval that is generally significantly longer than that for a single measurement cycle, and also to the continuous determination and monitoring of the mean arterial pressure.

BRIEF DESCRIPTION OF THE DRAWINGS

The above set forth and other features of the invention are made more apparent in the ensuing Detailed Description of the Invention when read in conjunction with the attached Drawings, wherein:

FIG. 3b is an end view of the transducer assembly of FIG. 3a;

FIG. 5 is a block diagram of apparatus constructed in accordance with the invention for interfacing to the cuff and transducer assembly of FIG. 2;

DETAILED DESCRIPTION OF THE INVENTION

Figure 2:
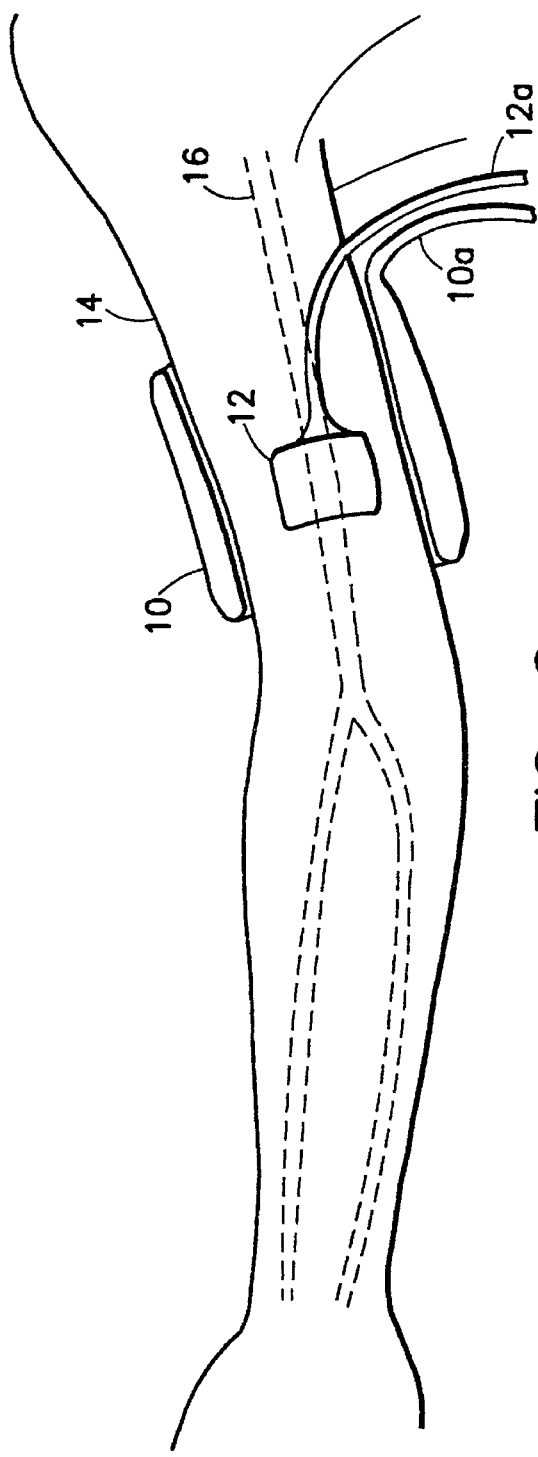
FIG. 2 illustrates a transducer assembly of the invention disposed beneath an inflatable cuff.

Referring to FIG. 2 in conjunction with FIG. 5, an inflatable cuff 10 and a transducer assembly 12 are affixed to, typically, an arm 14 of a subject. The transducer assembly 12 is positioned so as to be in the general vicinity of, and to generally overlie, the brachial artery 16. The cuff 10 is connected to a pump 18 by a conduit 10a whereby the pump 18 is enabled to pressurize and depressurize the cuff 10. Pressurization is accomplished with a compressible fluid, typically air. Outputs of the transducer assembly 12 are connected to a multiplexer (MUX) 20 via a cable 12a.

Figure 3B:
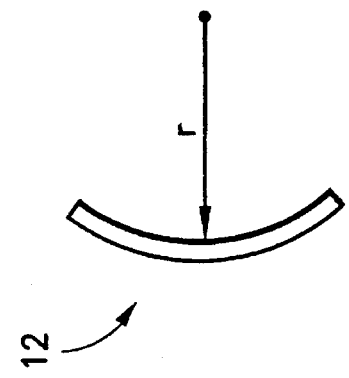
Figure 3A:
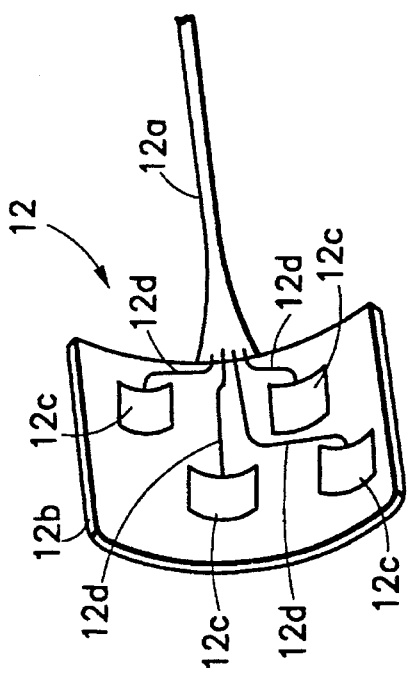
FIG. 3a is an elevational view illustrating the transducer assembly of FIG. 2.

As is seen more clearly in FIG. 3a, in one embodiment of the invention the transducer assembly 12 is comprised of a curved substrate 12b to which are affixed, on a concave surface thereof, a plurality of transducers 12c. Transducers 12c are preferably piezoelectric devices that generate a detectable voltage potential upon an application of a strain. During use, the strain is generated by the oscillations of the arterial blood flow through the partially occluded brachial artery 16. The generated voltage potential is conveyed from a given one of the transducers 12c by an associated conductor 12d that runs through the cable 12a to an input of the multiplexer 20.

In general, the response time of each transducer 12c is less than or equal to approximately 0.001 seconds, and the frequency response is within a range of approximately 0.2 Hz to approximately 50 Hz.

The apparatus of FIGS. 2 and 5 operates under the control of a processor 22, such as a microprocessor. As such, a memory 24 is bidirectionally coupled to the processor 22. The memory 24 contains a stored program for controlling the processor 22 to operate the apparatus in accordance with the methods of this invention, as illustrated in the flow charts of FIGS. 6 and 7. The processor 22 is also enabled to store data within, and retrieve data from, the memory 24 during the execution of the stored program. It should be realized that the memory 24 could be contained within the processor 22, and may not be a separately provided component.

The processor 22 is interfaced to the pump 18 via a pressure control signal line 18a. The processor 22 is thereby enabled to operate the pump 18 so as to controllably pressurize and depressurize the cuff 10. A measured pressure signal line 18b is provided from the pump 18 to an input of the processor 22 whereby the processor 22 is enabled to determine at any time the pressure that is being exerted upon the compressible fluid that pressurizes the cuff 10.

The processor 22 is also interfaced to the multiplexer 20 via a MUX address signal line 20a whereby the processor 22 is enabled to specify a particular one of the plurality of conductors 12d that is to be coupled from the input of the multiplexer 20 to an output 20b. In this manner the voltage potential appearing on a specified one of the plurality of the conductors 12d is passed through the multiplexer 20 to the output 20b.

Coupled to the output 20b is an analog to digital convertor (A/D) 26. A/D 26 operates in a conventional fashion to convert, in response to an activation of a SAMPLE signal line 26a, the voltage potential appearing at the input to a multi-bit digital output (D0-Dn). The value of n is a function of the desired measurement resolution. An eight bit output (n=7) is generally suitable for most applications. If required, an amplifier (not shown) may be interposed between the output of the MUX 20 and the input of the A/D 26. Alternately, an amplifier (not shown) may be provided for each of the inputs 12d before connection to the input of the MUX 20.

The digital output from A/D 26 is applied to a digital input port of the processor 22, thereby enabling the processor 22 to determine a magnitude of a voltage potential being generated by a particular one of the transducers 12c, as specified by the value of the MUX address 20a. The magnitude of the voltage potential indicates the magnitude of the oscillation resulting from the arterial blood flow through the partially occluded brachial artery 16. Such oscillations occur at a rate that is equal to the heart beat rate of the subject. The sampling rate of A/D 26 is set by the processor 22 so as to ensure that undersampling of the arterial pressure pulse does not occur, and that a sufficient number of samples are taken during an oscillation to enable a maximum amplitude of the oscillation to be determined.

The processor 22 is also bidirectionally coupled to a user interface 28 whereby the results of a blood pressure measurement cycle may be displayed to an operator, and whereby the operator is enabled to initiate a blood pressure measurement cycle. As an example, the user interface 28 includes an alphanumeric display 28a, such as an LED or LCD display, whereon the determined systolic (S) blood pressure, the determined diastolic (D) blood pressure, the determined mean arterial pressure (MAP), and the measured pulse rate (P) are displayed to the operator. The user interface 28 may also include a CRT or LCD display 28b for visually indicating in a graphical fashion the amplitudes of the oscillations measured by a selected one or ones of the transducers 12c. Also provided on the user interface 28 are switches 28c whereby the operator is enabled to, for example, initiate a single blood pressure measurement cycle, or specify that a continuous blood pressure measurement cycle be initiated.

Figure 1:
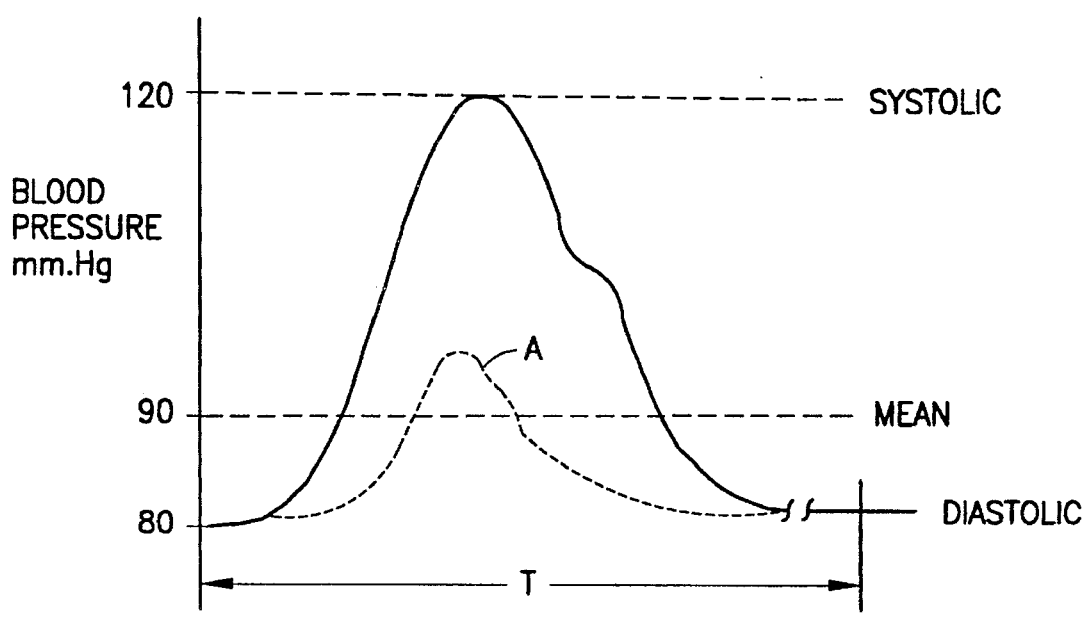
FIG. 1 is graph that depicts the variation in blood pressure over time, when measured with an invasive pressure sensor.
Figure 4:
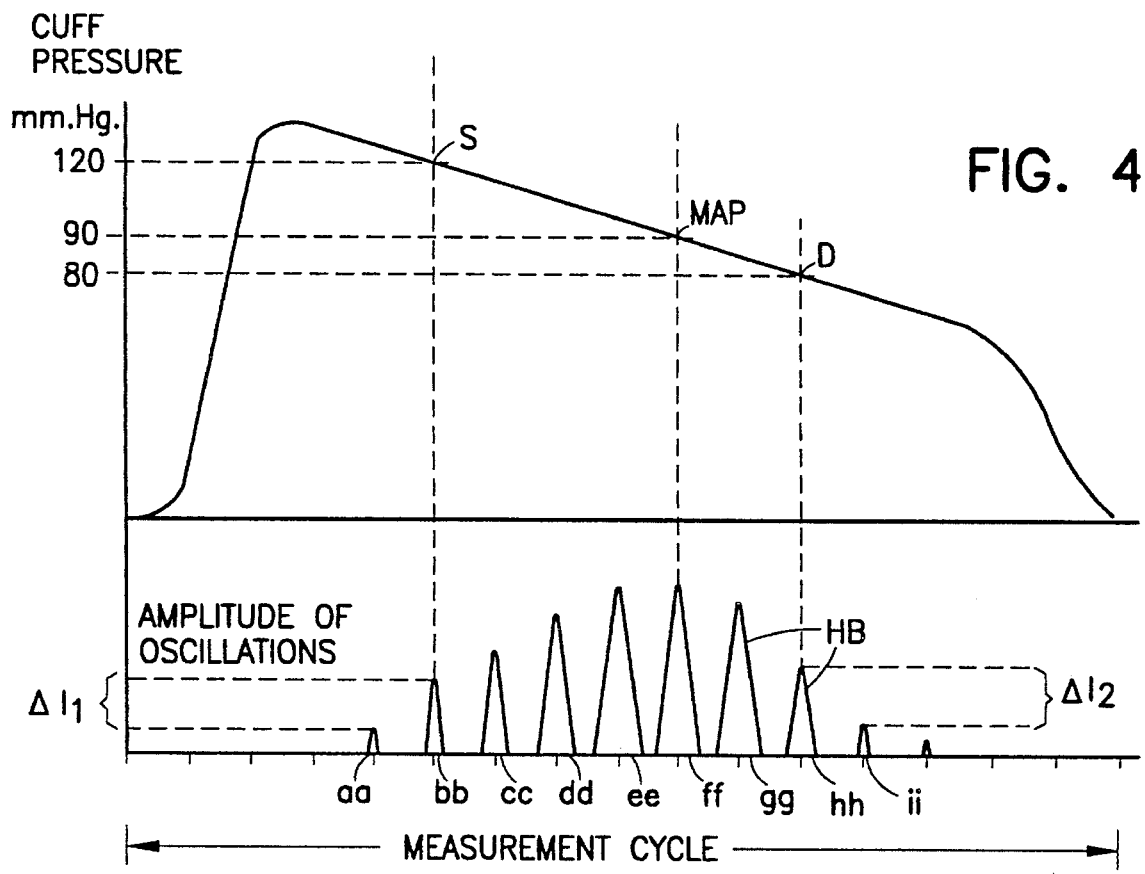
FIG. 4 is a graph that illustrates a blood pressure measurement cycle in accordance with the invention.
Figure 6:
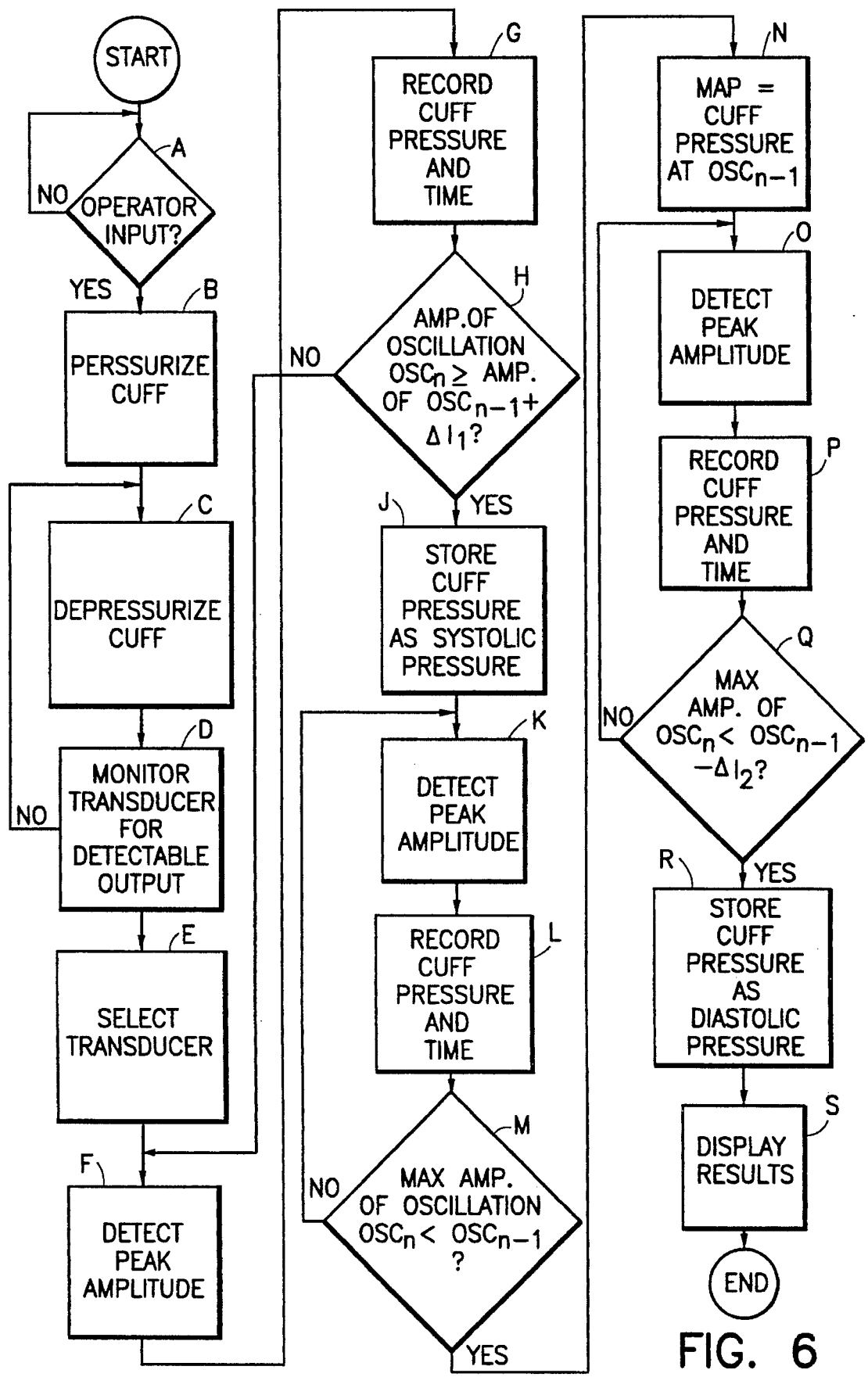
FIG. 6 is a flow chart that illustrates one embodiment of a method for operating the processor of FIG. 5 during the measurement of blood pressure.

In operation, and referring to a first method illustrated in the flow chart of FIG. 6 in conjunction with the graph of FIG. 4, the processor 22 idles in a loop waiting for operator input to initiate a blood pressure measurement cycle (Block A). If Yes at Block A, control passes to Block B wherein the processor 22 commands the pump 18 to pressurize the cuff 10 to a pressure that exceeds the normal systolic pressure. For example, the pump 18 is commanded, via pressure control signal line 18a, to pressurize the cuff 10 to a pressure that exceeds the typical systolic pressure by 30 mm.Hg. When the cuff is fully pressurized, the brachial artery 16 is completely occluded and no oscillations are sensed by any of the transducers 12c. At Block C the processor 22 commands the pump 18 to begin depressurizing the cuff 10. The cuff 10 may be depressurized in increments of pressure, such as 5 mm.Hg., or may be depressurized in a continuous fashion without significant pressure steps. At Block D the processor 22 reads individual ones of the transducers 12c until detectable signals are obtained from at least one of the transducers 12c, as indicated by the oscillation (aa) in the lower trace of FIG. 4. Each oscillation shown in the lower trace corresponds to one heart beat (HB). The detection of a signal indicates that the presently specified transducer is positioned sufficiently near to the brachial artery 16 so as to respond to the pulsation of arterial blood flow in the now partially occluded brachial artery. At Block E the processor 22 selects a transducer 12c having a highest amplitude signal, it being assumed that the selected transducer is optimally positioned for detecting the arterial blood pulsations. The method operates in a loop and continues to execute Blocks C and D until a suitable transducer is selected. Typically, the suitable transducer is selected as the transducer that indicates the highest amplitude of oscillation.

It is noted that after the initial oscillation (aa) is detected, it may be desirable to halt the decompression of the cuff 10 while scanning all of the transducers 12c to determine the transducer that is detecting the greatest amplitude of oscillation. In this manner the outputs of the transducers 12c are compared to one another while a constant compressive force is applied to the brachial artery.

The operation of the processor 22 at Blocks C, D, and E is facilitated by the construction of the transducer assembly 12 in accordance with an aspect of this invention. More specifically, the provision of a plurality of transducers 12c at various positions on the concave surface of the substrate 12a ensures that at least one transducer will be positioned at a location, relative to the brachial artery 16, for detecting arterial blood pulsations. Furthermore, each transducer 12c may have dimensions that are selected to be larger than the diameter of the brachial artery 16. By example, each transducer 12c can be provided with linear dimensions of approximately two centimeters when used with a brachial artery having a diameter of one centimeter. This use of relatively large transducers overcomes the constraints imposed on many conventional tonometric type systems that employ one or more small transducers that must be accurately and precisely positioned over an artery of interest, and maintained in that position during the measurement. However, the use of one or more transducers having dimensions that are equal to or smaller than the artery is also within the scope of this invention.

In addition, and in accordance with an aspect of this invention, the substrate 12a may be provided with a radius of curvature (r), as best seen in FIG. 3b, that is selected to correspond to the curvature of the limb to which the transducer assembly 12 is applied. The substrate 12a is thus preferably comprised of a non-electrically conductive rigid or semi-rigid material, such as a thermoplastic, so as to maintain the radius of curvature. The use of a semi-rigid material enables the curvature of the substrate 12a to change as a result of the compressive force exerted by the cuff, and to thus accommodate itself to the curvature of the limb.

In accordance with this aspect of the invention, various transducer assemblies may be provided, thereby enabling the operator to select a transducer assembly having a radius of curvature that best matches the curvature of the limb of the subject. As such, a number of transducer assemblies 12 may be provided, differing from one another by the radius of curvature, for use with children and adults within various weight ranges. Of course, the size of the individual transducers 12c may be scaled accordingly, in that the brachial artery will differ in diameter between, by example, an adult male and a small child.

However, if desired the substrate could be comprised of a flexible material that is wrapped totally or partially about the limb. In like manner, the substrate may comprise the inner wall of the cuff 10.

Having acquired an optimal one of the transducers 12c at Blocks C–D–E, the method then executes Blocks F–G–H where the selected transducer is monitored, while continuing to deflate the cuff 10, until the amplitude of oscillation rises to a value that exceeds the initial value of oscillation (aa) by a predetermined first increment $\Delta I_1$ (FIG. 4). As an example, the predetermined first increment may be 100% of the amplitude of the oscillation (aa).

More particularly, Blocks F–G–H are a monitoring loop wherein the processor 22 continues to reduce the cuff pressure while detecting the maximum amplitude of each successive oscillation recorded by the selected transducer 12c (Block F). When the maximum amplitude of an oscillation is detected, the processor 22 records the pressure of the cuff 10 at the time of maximum amplitude and the time at which the maximum amplitude occurred (Block G). For a given oscillation ($OSC_n$), the processor 22 compares at Block H the maximum amplitude to the sum of the maximum amplitude of oscillation $OSC_{n-1}$ and the predetermined first increment $\Delta I_1$. If the maximum amplitude of oscillation $OSC_n$ is less than the maximum amplitude of the previous oscillation, plus the predetermined first increment, control returns to Block F. If the result of the comparison at Block H indicates Yes, then control passes to Block J. This will occur for the oscillation (bb).

The oscillation identified as exceeding the initial oscillation by the predetermined first increment (designated as (bb)) is recorded, and at Block J the cuff pressure recorded for the maximum amplitude of oscillation (bb) is stored as the systolic pressure (Ṡ).

Blocks K–L–M are a monitoring loop wherein the processor 22 continues to reduce the cuff pressure while detecting the maximum amplitude of each successive oscillation recorded by the selected transducer 12c (Block K). When the maximum amplitude of an oscillation is detected, the processor 22 records the pressure of the cuff 10 at the time of maximum amplitude and the time at which the maximum amplitude occurred (Block L). For a given oscillation ($OSC_n$), the processor 22 compares at Block M the maximum amplitude to the maximum amplitude recorded for the preceding oscillation ($OSC_{n-1}$). If the maximum amplitude of oscillation ($OSC_n$) is greater than the maximum amplitude of oscillation ($OSC_{n-1}$), the control returns to Block K. Such would be the case for oscillations (cc), (dd), (ee) and (ff) of FIG. 4. If the result of the comparison at Block M indicates Yes, indicating that the most recent oscillation has a amplitude that is less than the amplitude of the preceding oscillation, then control passes to Block N. This will occur for the oscillation (gg).

At Block N the processor 22 recalls the cuff pressure that was recorded when the maximum amplitude of oscillation (ff) was detected. The recalled cuff pressure is stored as the Mean Arterial Pressure (MAP). That is, the cuff pressure that corresponds to the oscillation having a greatest maximum amplitude is correlated with the MAP.

Blocks O–P–Q are also a monitoring loop wherein the processor 22 continues to reduce the cuff pressure while detecting the maximum amplitude of each successive oscillation recorded by the selected transducer 12c (Block O). When the maximum amplitude of an oscillation is detected, the processor 22 records the pressure of the cuff 10 at the time of maximum amplitude and the time at which the maximum amplitude occurred (Block P). For a given oscillation ($OSC_n$), the processor 22 compares at Block Q the maximum amplitude to the difference between the maximum amplitude of oscillation $OSC_{n-1}$ and the predetermined second increment $\Delta I_2$. If the maximum amplitude of oscillation $OSC_n$ is greater than the maximum amplitude of the previous oscillation, minus the predetermined second increment, control returns to Block O. If the result of the comparison at Block I indicates Yes, then control passes to Block R.

This will occur for the oscillation (ii). As an example, the predetermined second increment may be 100% of the amplitude of the preceding oscillation, in this case the oscillation (hh).

The oscillation identified as being less than the previous oscillation by the predetermined second increment is recorded, and at Block R the cuff pressure recorded for the maximum amplitude of oscillation (hh) is stored as the diastolic pressure (D).

At Block S the processor 22 recalls the stored systolic (S), MAP, and diastolic (D) pressures and provides them to the alphanumeric display 28a of the user interface 28. The processor 22 is also enabled, based on the recorded times that maximum oscillation amplitudes occurred, to determine the pulse rate (P) and to also provide the pulse rate to the user interface 28. By example, an average of the times between adjacent peak amplitudes is determined, and the result is divided into 60 seconds. If desired, the processor 22 can also recall the stored maximum amplitudes of the oscillations, suitably scale same in amplitude and time, and generate the graphical display for the CRT or LCD display 28b.

Figure 7:
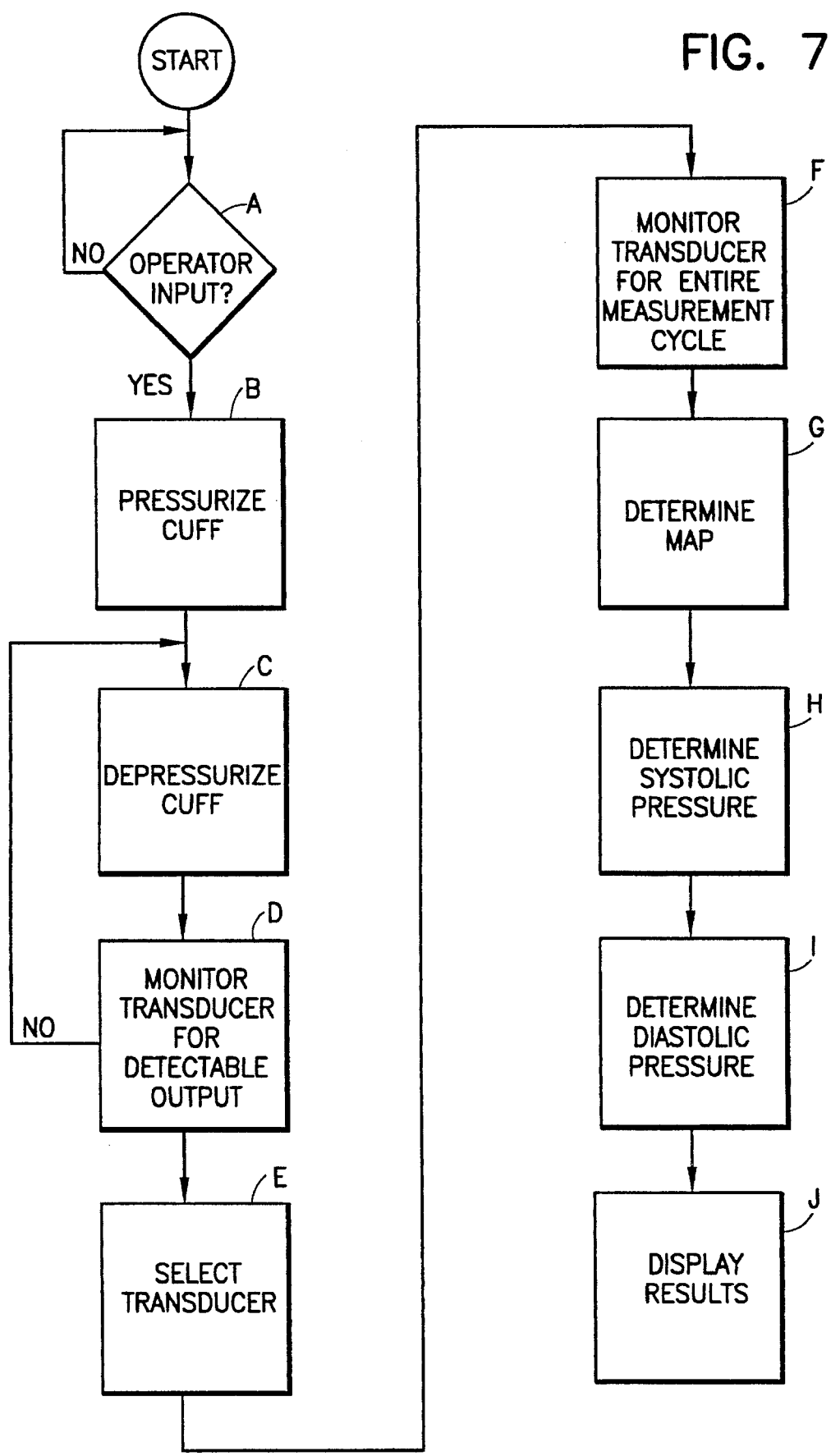
FIG. 7 is a flow chart that illustrates another embodiment of a method for operating the processor of FIG. 5 during the measurement of blood pressure.

FIG. 7 depicts a further method in accordance with the teaching of this invention. Blocks A–E are performed identically to Blocks A–E of FIG. 6 so as to select a suitable one of the transducers 12c. At Block F the processor 22 monitors the output of the selected transducer for the entire blood pressure measurement cycle so as to detect and store the maximum amplitude, and the time of occurrence, for each pressure oscillation. When a maximum amplitude is detected, the cuff pressure is measured and stored. At Block G the oscillation having the largest stored maximum amplitude is determined, and the corresponding stored cuff pressure is correlated with the MAP. Next, at Block H a predetermined percentage of the maximum oscillation amplitude, such as 50%, is determined, and a cuff pressure corresponding to the pressure pulse having a maximum amplitude that is within a predetermined range of the percentage is correlated with the systolic pressure. If no pressure pulse has a maximum amplitude within the predetermined range, then two adjacent pulses that bracket the percentage can be employed, and the cuff pressure is extrapolated from the cuff pressures corresponding to the two adjacent pulses. Instead of using a fixed percentage, a determination of a change in a rate of change of the maximum pulse amplitudes can be employed instead.

At Block I a predetermined percentage of the maximum oscillation amplitude, such as 50%, is determined, and a cuff pressure corresponding to the pressure pulse having a maximum amplitude that is within a predetermined range of the percentage is correlated with the diastolic pressure. As in Block H, if no pressure pulse has a maximum amplitude within the predetermined range, then two adjacent pulses that bracket the percentage can be employed, and the cuff pressure is extrapolated from the cuff pressures corresponding to the two adjacent pulses. Also as in Block H, a determination of a change in a rate of change of the maximum pulse amplitudes can be employed instead of the fixed percentage.

At Block J the results are displayed, as in Block S of FIG. 6. The pulse rate may also be determined and displayed, as previously described.

It can be appreciated that the method of FIG. 6 enables operation in real time during a blood pressure measurement cycle, whereas the method of FIG. 7 accumulates readings over the measurement cycle and then subsequently determines the MAP, systolic, and diastolic pressures.

It is within the scope of the invention to temporarily maintain the cuff pressure within a range of pressures, for example ±10%, about the pressure that correlates with the MAP determined at Block N of FIG. 6 or Block G of FIG. 7, and to continually update the display 28a, for each heart beat, with the MAP. That is, the processor 22 operates in a loop so as to vary the cuff pressure to obtain oscillations having a maximum amplitude. As a result, the MAP is determined and displayed for each heart beat over a period of time. This mode of operation can be entered in response to one of the switches 28c.

Figure 8:
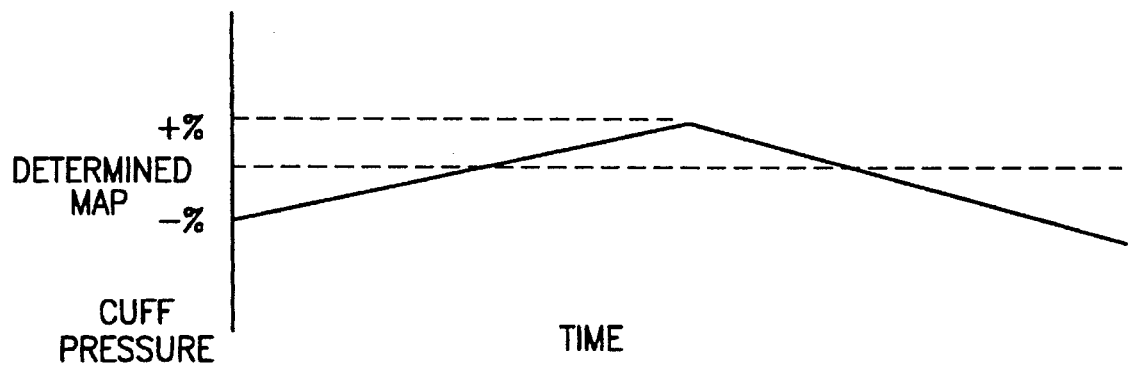
FIG. 8 depicts an exemplary cuff pressure variation cycle about the determined MAP, when executing a method of continuous MAP monitoring.

In this mode of operation, either the method of FIG. 6 or FIG. 7 is first executed so as to determine the MAP. After this calibration procedure, the cuff 10 is inflated to the pressure that corresponds to the determined MAP, and the cuff pressure is then slowly varied above and below the determined MAP pressure (FIG. 8) while the processor 22 determines the maximum amplitude of the pressure pulses received from the selected transducer 12c. The frequency of the pressure variation is selected to be significantly less than the heart rate. For example, for a heart rate of 60 beats per minute a suitable frequency of cuff pressure variation is 0.2 Hz. For each determined pressure pulse of greatest maximum amplitude, the corresponding cuff pressure is reported as the MAP. This mode of operation can be especially beneficial during a surgical procedure, in that it enables the continuous determination and monitoring of the MAP over an interval of time that is longer than a typical blood pressure measurement interval.

Figure 9A:
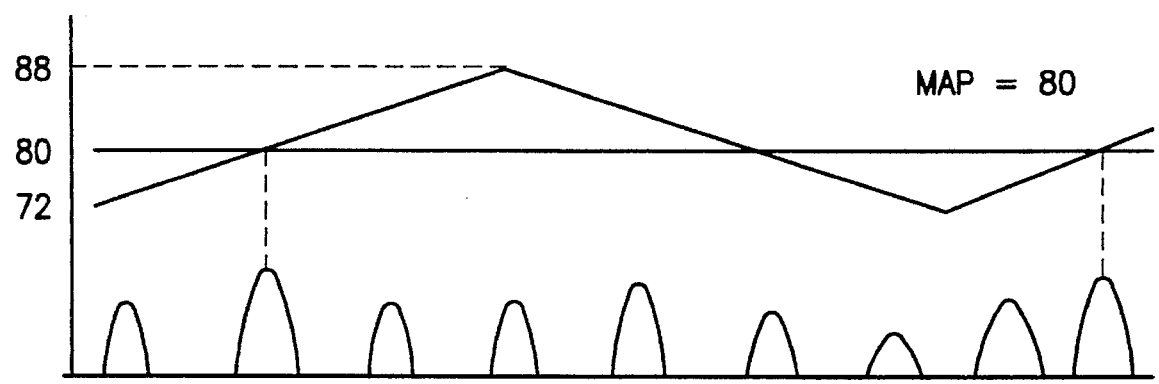
FIGS. 9a–9c are three examples corresponding to the cuff pressure variation cycle of FIG. 8.
Figure 9B:
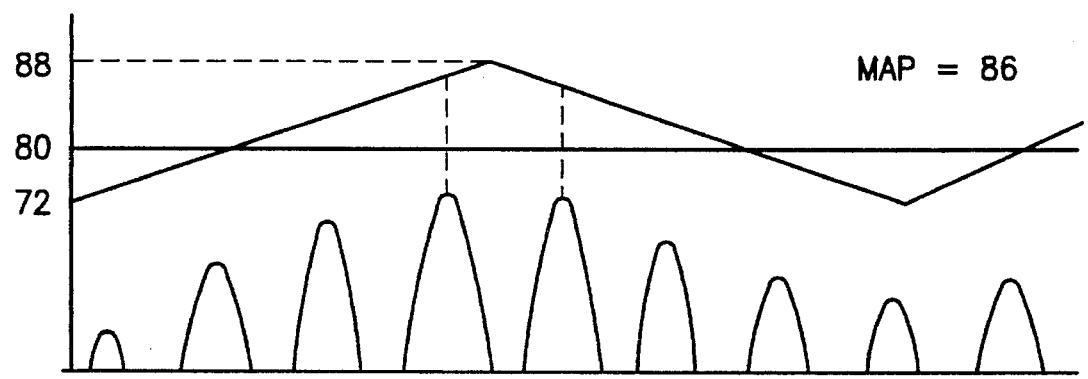
Figure 9C:
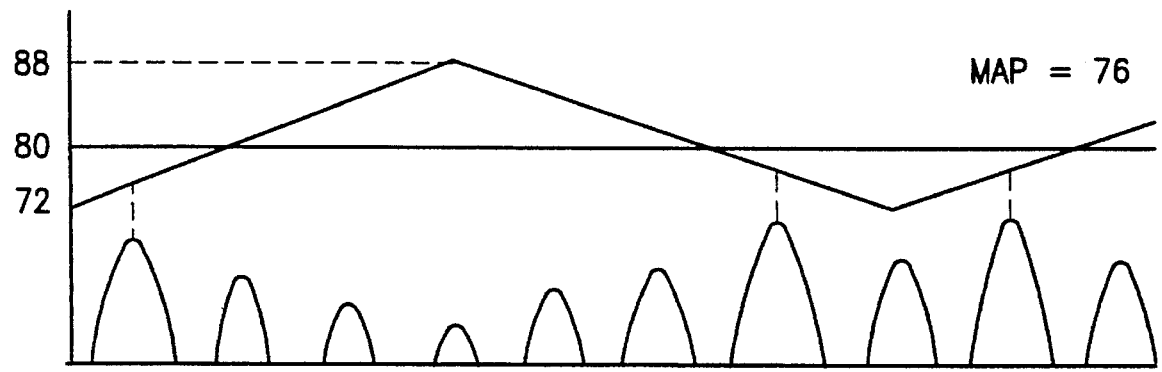

FIGS. 9a–9c are an example where the MAP baseline pressure is 80 mm Hg, and wherein the cuff pressure is varied plus and minus ten percent around the MAP baseline pressure (72 mm Hg to 88 mm Hg).

FIG. 9a illustrates the case where the MAP remains substantially constant. As can be seen, the greatest maximum amplitude of the pressure pulses occur for a cuff pressure of 80 mm Hg. At other cuff pressures the maximum amplitudes of the pressure pulses are reduced. This reduction in maximum amplitude of the pressure pulses above and below the MAP pressure corresponds to, by example, the reduced amplitudes of the pulses (ee) and (gg), respectively, that bracket the pulse (ff) in FIG. 4.

FIG. 9b illustrates the case where the MAP has increased from the originally established baseline pressure, while FIG. 9c illustrates the case where the MAP has decreased from the originally established baseline pressure. In both of these cases the MAP remains within the plus and minus 10 percent cuff pressure variation. The processor 22 is enabled to detect this change in MAP over several pressure pulses and, if desired, shift the baseline pressure either upwardly or downwardly so as to correspond to the new value of MAP.

If the MAP changes during the monitoring period, such that it lies above or below the varying range of cuff pressures, the cuff 10 can be deflated and another measurement cycle (FIG. 6 or 7) initiated, either manually or automatically, so as to determine the new value of MAP. The cuff 10 is then inflated to the newly determined MAP pressure and the continuous MAP measurement cycle is re-initiated.

Alternatively, the processor 22 is operable to incrementally vary the baseline cuff pressure either upwardly or downwardly so as to accommodate a sudden increase or decrease in the MAP, without executing a calibration measurement cycle. For either technique, it may also be desirable to provide an audible and/or visual indication at the user interface 28 to notify an operator of the sudden change in the MAP.

It is also within the scope of the invention to provide a continuous indication of blood pressure by inflating the cuff 10 at low pressures and then sensing the oscillations with the transducer assembly 12. The amplitude of the oscillations are proportional to the arterial blood pressure.

Figure 10:
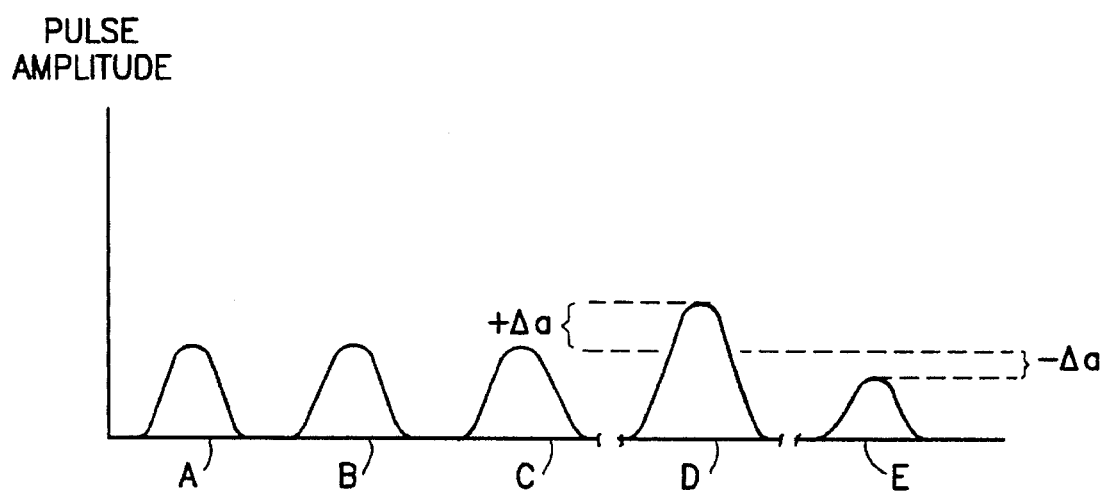
FIG. 10 illustrates a method of continuous blood pressure determination for a cuff pressure that is maintained at a pressure less than the diastolic pressure.

In this mode of operation either the method of FIG. 6 or FIG. 7 is first executed so as to determine at least the systolic and the diastolic blood pressures. After this calibration procedure, the cuff 10 is inflated to a pressure that is less than the determined diastolic pressure. The cuff pressure is then maintained at this level while the processor 22 determines the maximum amplitude of the pressure pulses received from the selected transducer 12c (FIG. 10). The cuff pressure is preferably maintained above the venous pressure (normally below 15 Torr) and below the determined diastolic pressure. The maximum amplitudes of the pressure pulses are recorded, now significantly reduced due to the reduction in cuff pressure below the diastolic pressure, and are correlated with, by example, the previously measured systolic pressure. As seen in FIG. 10, the pulses A, B, and C are all of approximately the same amplitude and are correlated with the previously measured systolic pressure of, by example, 130 mm Hg. At a subsequent time the maximum measured amplitude increases (pulse D). The percentage change (+$\Delta$a) is translated into a corresponding percentage increase in the systolic pressure of from, for example, 130 mm Hg to 145 mm Hg, and reported via the user interface 28. Likewise, and as is Shown for the pulse E, a subsequent decrease in pulse amplitude is translated into a corresponding decrease in the systolic pressure.

If desired, for a first increase or decrease of the pulse amplitude above a predetermined threshold, for example 10%, the measurement cycle of FIG. 6 or 7 can be re-initiated so as to determine absolute values for the new systolic and diastolic pressures. The newly acquired values are then employed to calibrate the translation process. For example, an increase in pulse amplitude of 17% may be found to correspond to a rise in the systolic pressure from 130 mm Hg to 150 mm Hg. That is, a 17% increase in pulse amplitude is found to correspond to a 20 mm Hg increase in the systolic pressure.

In that the venous blood flow is not completely occluded by the method of sub-diastolic blood pressure measurement described above, this method can be utilized for significantly longer periods of time than can the method of continuous MAP determination described previously.

While the invention has been particularly shown and described with respect to presently preferred embodiments thereof, it will be understood by those skilled in the art that changes in form and details may be made therein without departing from the scope and spirit of the invention.

What is claimed is:

1. Apparatus for determining blood pressure within an artery of a subject, comprising in combination:

a cuff adapted for being placed around an extremity of the subject;

means for controllably pressurizing and depressurizing said cuff, including means for sensing a pressure within said cuff;

a blood pressure sensor assembly comprising a substrate and at least one pressure transducer means disposed upon said substrate for being urged against the extremity by said cuff, said at least one pressure transducer means being capable of sensing an arterial blood pressure oscillation; and means, having inputs coupled to an output of said cuff pressure sensing means and also to an output of said at least one pressure transducer means, for determining a magnitude of the systolic blood pressure, a magnitude of the diastolic blood pressure, and a magnitude of a mean arterial blood pressure of the subject as a function of measured amplitudes, and relationships between measured amplitudes, of a plurality of arterial blood pressure oscillations and also in accordance with a sensed pressure within said cuff at a time of occurrence of each of said plurality of arterial blood pressure oscillations.

2. Apparatus as set forth in claim 1 wherein said at least one pressure transducer means has linear dimensions greater than a diameter of the artery.

3. Apparatus as set forth in claim 1, wherein there are a plurality of pressure transducer means, wherein said determining means includes means for individually measuring said output of each of said pressure transducer means, and further includes means for selecting one of said outputs for use in determining the magnitude of the systolic, diastolic, and mean arterial pressures.

4. Apparatus for determining blood pressure within an artery of a subject, comprising in combination:

a cuff adapted for being placed around an extremity of the subject;

means for controllably pressurizing and depressurizing said cuff, including means for sensing a pressure within said cuff;

a blood pressure sensor assembly comprising a substrate and at least one pressure transducer means disposed upon said substrate for being urged against the extremity by said cuff, said at least one pressure transducer means being capable of sensing an arterial blood pressure oscillation; and means, having inputs coupled to an output of said cuff pressure sensing means and also to an output of said at least one pressure transducer means, for determining a magnitude of the systolic blood pressure, a magnitude of the diastolic blood pressure, and a magnitude of a mean arterial blood pressure of the subject as a function of a measured amplitude of at least one arterial blood pressure oscillation and a sensed pressure within said cuff at a time of occurrence of said at least one arterial blood pressure oscillation; wherein said substrate has a curvature selected to conform to a curvature of the extremity and is adapted for having a concave surface thereof maintained in contact with said extremity when placed between said cuff and said extremity, wherein said at least one pressure transducer means is disposed upon said concave surface.

5. A blood pressure measuring assembly, comprising:

a substrate having a predetermined radius of curvature selected for corresponding to a curvature of an extremity of a subject, said substrate having an inner concave surface and an outer surface;

a plurality of blood pulse sensor elements disposed upon said inner surface of said substrate, said inner surface being a surface that contacts the extremity during the use of the assembly, each of said blood pulse sensor elements having a size that is a function of a diameter of an artery within the extremity; and an inflatable cuff having a length suitable for wrapping around the extremity for urging said inner surface of said substrate against the extremity.

6. An assembly as set forth in claim 5 wherein the size of each of the blood pressure sensor elements is selected to be larger than the diameter of the artery.

7. Apparatus for determining blood pressure within an artery of a subject, comprising in combination:

a cuff adapted for being placed around an extremity of the subject;

means for controllably pressurizing and depressurizing said cuff, including means for sensing a pressure within said cuff;

a blood pressure sensor assembly comprising a substrate and at least one pressure-responsive transducer disposed upon said substrate for being urged against the extremity by said cuff, said at least one pressure-responsive transducer being capable of sensing an arterial blood pressure oscillation; and means, having inputs coupled to an output of said cuff pressure sensing means and also to an output of said at least one pressure-responsive transducer, for recording pressure oscillations and corresponding cuff pressures and for determining a magnitude of the systolic blood pressure, a magnitude of the diastolic blood pressure, and a magnitude of a mean arterial blood pressure of the subject as a function of said recorded pressure oscillations and said corresponding cuff pressures; and wherein said means for controllably pressurizing and depressurizing said cuff is thereafter controlled to maintain the cuff pressure within a range of pressures about the determined mean arterial pressure for monitoring the mean arterial pressure of the subject in cooperation with the operation of said recording and determining means.

8. Apparatus as set forth in claims 7 wherein said means for controllably pressurizing and depressurizing is controlled to periodically vary the cuff pressure above and below the determined mean arterial pressure at a rate that is less than the heart rate of the subject.

9. Apparatus as set forth in claim 7 wherein said means for controllably pressurizing and depressurizing is controlled to vary the cuff pressure so as to accommodate a determined change in the mean arterial pressure.

10. Apparatus as set forth in claim 7 and further comprising means for providing an indication to an operator of the apparatus of a determined change in the mean arterial pressure.

11. Apparatus for determining blood pressure within an artery of a subject, comprising in combination:

a cuff adapted for being placed around an extremity of the subject;

means for controllably pressurizing and depressurizing said cuff, including means for sensing a pressure within said cuff;

a blood pressure sensor assembly comprising a substrate and at least one pressure transducer means disposed upon said substrate for being urged against the extremity by said cuff, said at least one pressure transducer means being capable of sensing an arterial blood pressure oscillation; and means, having inputs coupled to an output of said cuff pressure sensing means and also to an output of said at least one pressure transducer means, for determining a magnitude of the systolic blood pressure, a magnitude of the diastolic blood pressure, and a magnitude of a mean arterial blood pressure of the subject as a function of measured amplitudes, and relationships between measured amplitudes, of a plurality of arterial blood pressure oscillations and also in accordance with a sensed pressure within said cuff at a time of occurrence of each of said plurality of arterial blood pressure oscillations, wherein said substrate has a curvature selected to conform to a curvature of the extremity and is adapted for having a concave surface thereof maintained in contact with said extremity when placed between said cuff and said extremity, wherein said at least one pressure transducer means is disposed upon said concave surface.

* * * * *